United States Patent [19]

Clapham

[11] Patent Number: 4,607,634

[45] Date of Patent: Aug. 26, 1986

[54] ANAESTHETIC VAPORIZER

[75] Inventor: Thomas R. Clapham, Skipton, England

[73] Assignee: The BOC Group plc, Windlesham, England

[21] Appl. No.: 647,950

[22] Filed: Sep. 6, 1984

[30] Foreign Application Priority Data

Sep. 12, 1983 [GB] United Kingdom ............... 8324313

[51] Int. Cl.4 ............................................ A61M 15/00
[52] U.S. Cl. ......................... 128/203.25; 128/204.14; 261/DIG. 65
[58] Field of Search ..................... 128/204.14, 204.13, 128/200.11, 203.25, 205.11, 205.24; 137/625.29, 625.3, 625.32, 599; 261/DIG. 65, 64 R

[56] References Cited

U.S. PATENT DOCUMENTS 2,998,023 8/1961 Campbell et al. .................. 137/599
3,661,368 5/1972 Metivier ......................... 128/203.25

*Primary Examiner*—Henry J. Recla
*Attorney, Agent, or Firm*—Roger M. Rathbun; Larry R. Cassett

[57] ABSTRACT

An anaesthetic vaporizer of the by-pass type in which the concentration of anaesthetic vapor in the gas leaving the vaporizer is controlled by a valve arrangement which is capable of varying the resistance to gas flow of a second or by-pass stream which effectively alters the proportion in which the carrier gas is divided between said second by-pass stream and a first stream which passes through a vaporizing chamber. The valve arrangement includes a valve body 32 rotatable within a valve housing 30 having three spaced inlet holes 33, 35, 37 and an outlet hole 40 for the second gas stream. Rotary movement of the valve body 32 variously covers or uncovers the inlet holes 33, 35 and 37 to vary the resistance to the flow of the second stream from the inlet holes to the outlet hole 40 of the housing 30.

3 Claims, 8 Drawing Figures

ANAESTHETIC VAPORIZER

BACKGROUND OF THE INVENTION

The present invention relates to anaesthetic vaporisers which are devices for mixing the vapour of a volatile liquid anaesthetic agent with a carrier gas (which term is to be understood to include gas mixtures), for subsequent administration to a patient.

Throughout this specification the term "anaesthetic" is intended to embrace both anaesthetics and analgesics.

Anaesthetic vaporisers are known in which the carrier gas supplied to the vaporiser is divided into two streams. One stream is directed through a vaporising chamber containing volatile liquid anaesthetic where it becomes saturated with the vapour of the anaesthetic. The second stream by-passes the vaporising chamber. The two streams subsequently reunite downstream of the vaporising chamber and then pass through an outlet of the vaporiser for administration to the patient.

Such anaesthetic vaporisers are know generally as "by-pass" vaporisers and an example of such a by-pass vaporiser is described in UK Pat. No. 968054.

UK Pat. No. 968054 describes a by-pass vaporiser in which the concentration of anaesthetic vapour in the gas leaving the vaporiser is controlled by a valve arrangement which is capable of varying the resistance to gas flow of the second or by-pass stream. The valve arrangement has the effect of altering the proportions in which the carrier gas is divided into said two streams. This known by-pass vaporiser has been found to be successful in medical applications in that the concentration of anaesthetic vapour in the gas leaving the vaporiser can be controlled accurately.

However, this known by-pass vaporiser does have the disadvantage that the valve arrangement is complicated and requires very accurate machining and fitting and is thus expensive to produce. Further, the vaporiser needs to be monitored by a skilled anaesthetist since the concentration of anaesthetic is infinitely variable between set limits.

SUMMARY OF THE INVENTION

It is an aim of the present invention to provide an anaesthetic vaporiser of the "by-pass" type having a valve arrangement which is simple and economic to manufacture and which is capable of being used in field or emergency applications when skilled personnel may not be present.

According to the present invention, an anaesthetic vaporiser comprises a body part including a vaporising chamber for volatile liquid anaesthetic, an inlet into and an outlet from the body part for the passage therethrough of a first stream of a carrier gas, and a valve arrangement for dividing the carrier gas between said first stream and a second stream which by-passes the body part, the valve arrangement including a valve body rotatable within a housing having at least two spaced inlets and an outlet for the passage therethrough of the second stream, rotary movement of the valve body variously covering and uncovering the inlet(s) to vary the resistance to flow of the second stream from the inlet(s) to the outlet of the housing.

BRIEF DESCRIPTION OF DRAWINGS

An embodiment of the invention will now be described by way of example, reference being made to the Figures of the accompanying diagrammatic drawings in which.

DESCRIPTION OF PREFERRED EMBODIMENT

Figure 1:
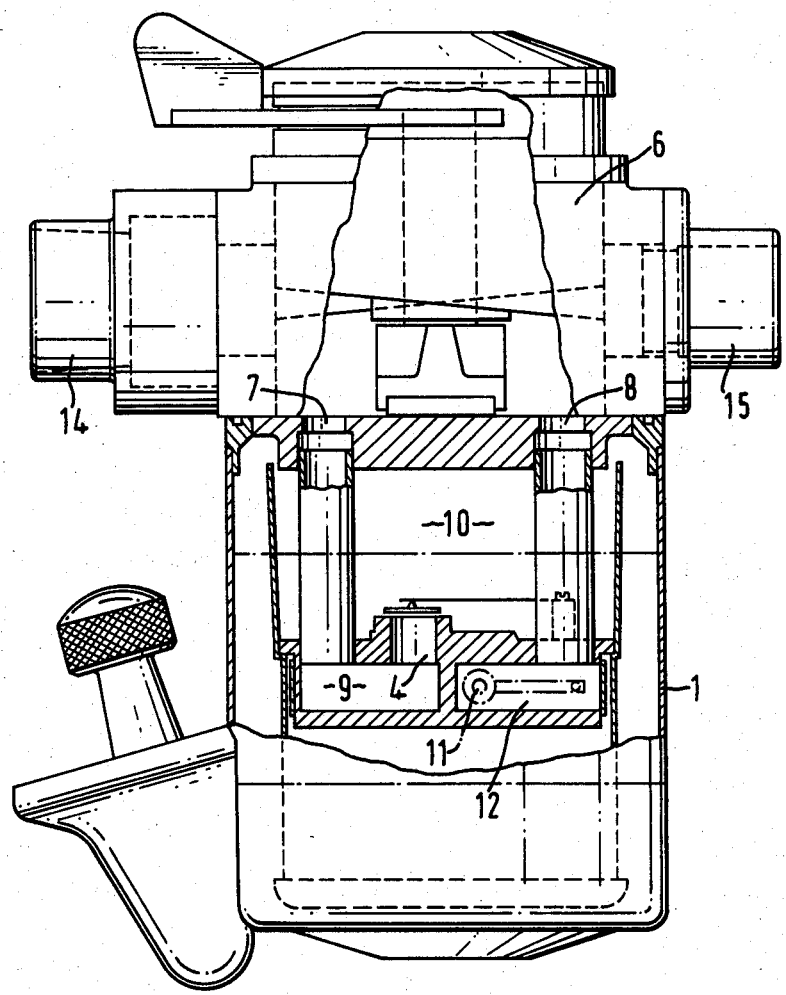
FIG. 1 is a part sectional elevation of the prior art vaporiser.
Figure 2:
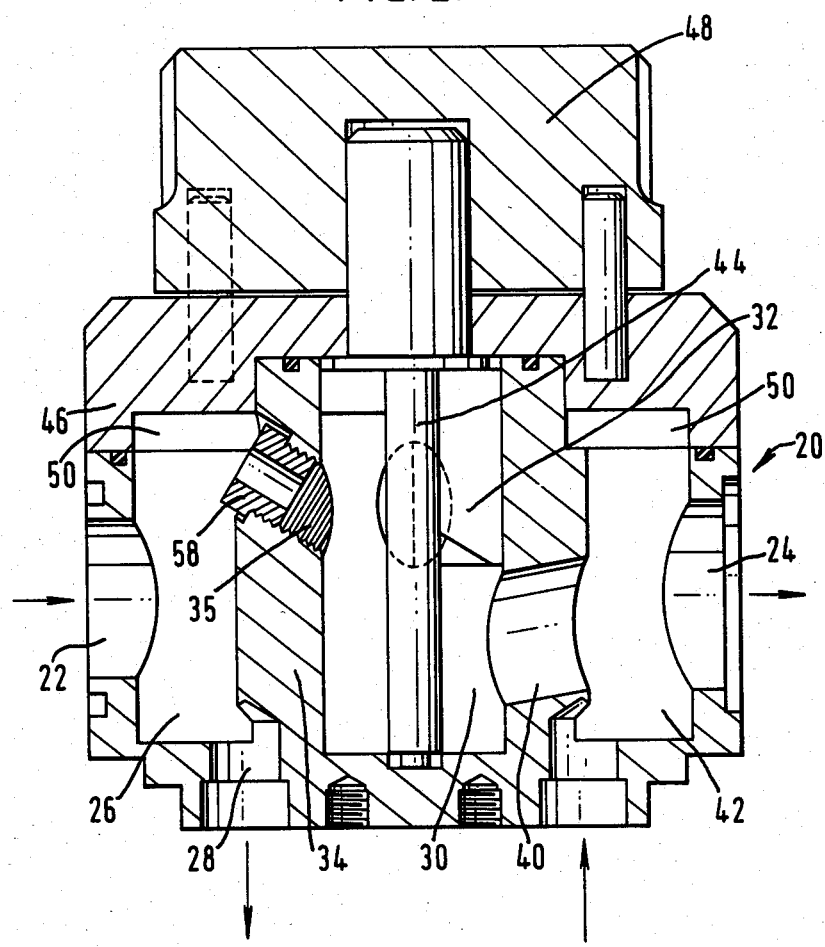
FIG. 2 is an elevation of a valve arrangement forming part of the anaesthetic vaporiser of the present invention.
Figure 3:
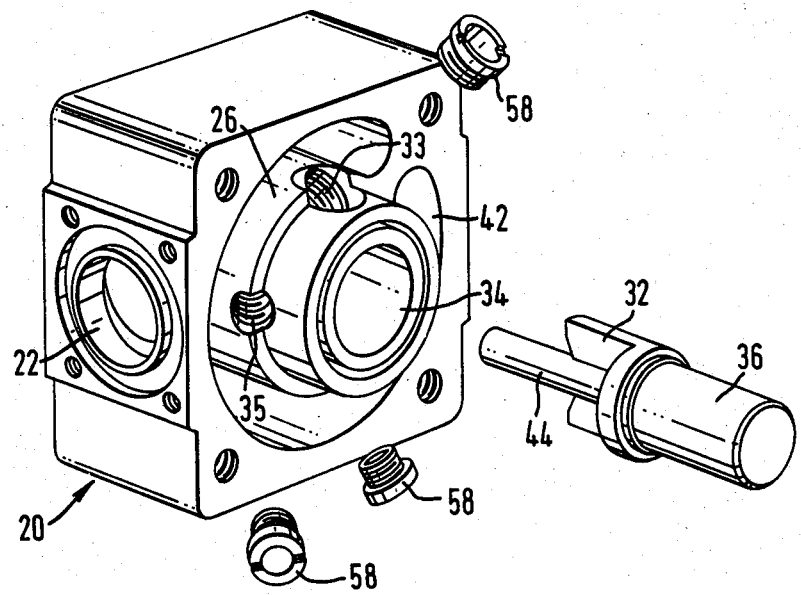
FIG. 3 is an exploded perspective view of the valve arrangement of FIG. 2 with a cover removed.
Figure 4:
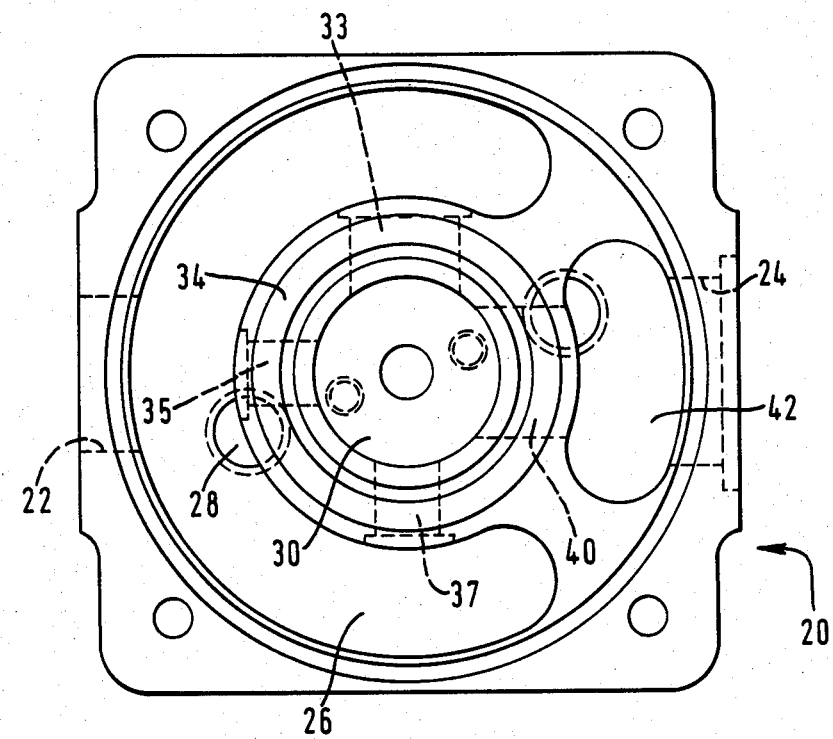
FIG. 4 is a plan view of a valve casing forming part of the valve arrangement of FIG. 2.
Figure 5:
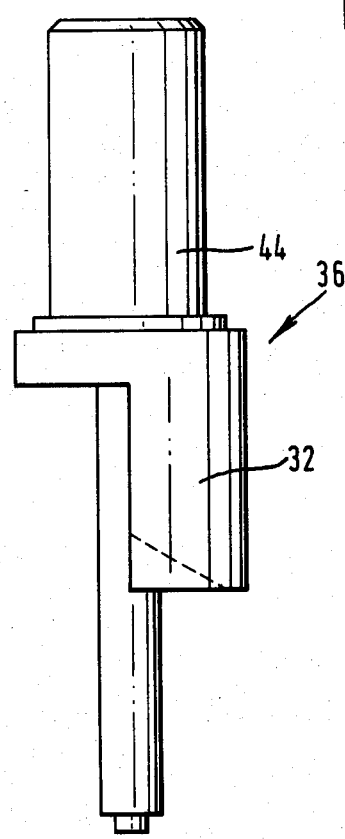
FIG. 5 is an elevation of a valve member forming part of the valve arrangement of FIG. 2.

Referring first to FIG. 1, this illustrates a known vaporiser of the by-pass type which includes a body part 1 enclosing a vaporising chamber 10 containing a volatile liquid anaesthetic. Carrier gas enters the vaporiser at main inlet 14 and is divided into two streams. One stream is directed through inlet port 7, inlet chamber 9, and port 4 into vaporising chamber 10. Said one stream then leaves vaporising chamber 10 together with anaesthetic vapour via port 11, chamber 12 and outlet port 8. From outlet port 8 the carrier gas/vapour enters a valve casing 6 where it is reunited with a second by-pass stream before leaving the vaporiser via main outlet 15.

The anaesthetic vaporiser of the present invention may have a body part 1 as described and illustrated with respect to FIG. 1.

Referring now to FIGS. 2 to 8, a valve casing 20 arranged to be mounted on the body part 1 has an inlet 22 for carrier gas and an outlet 24 from which carrier gas and anaesthetic vapour can pass for administration to a patient. Inlet 22 communicates with a chamber 26 of U-configuration in plan view (see FIG. 4). A passage 28 extends between the chamber 26 and an inlet (ref. 7 in FIG. 1) to the body part 1. The chamber 26 partially surrounds a valve housing 30 of cylindrical configuration containing a rotatable valve body 32. Extending through a wall 34 between the chamber 26 and housing 30 are three angularly spaced, threaded inlet holes 33, 35 and 37 each having a removable threaded jet 58 screwed therein. A further outlet hole 40 in the wall 34 extends between the housing 30 and a chamber 42 communicating with the outlet 24. Also communicating with the chamber 42 is an outlet (ref. 8 in FIG. 1) from the body part 1.

The valve body 32 forms part of a valve member 36 and has a cross-sectional shape which is segmental in configuration. The valve body 32 is fixed for rotation with a spindle 44 extending through a cover 46 mounted on the valve casing 20. A knob 48 is attached to the upper (as shown) end of the spindle 44.

The lower (as shown) surface of the cover 46 is counterbored to define a shallow passageway 50 which extends around the wall 34 from the inlet 22 to the outlet 24 for carrier gas.

It will be understood that the valve casing 20 is bolted or otherwise attached to a body part 1 and the cover 46 is bolted or otherwise attached to the valve casing 20.

In operation, carrier gas enters the valve casing 20 via inlet 22. From inlet 22 the carrier gas enters chamber 26 and a small percentage by volume of the carrier gas will then enter passageway 50 and flow therealong into chamber 42 and hence leave the vaporiser at outlet 24.

Depending on the resistance to flow through the valve casing 20, some of the carrier gas, that is, the first stream, will leave chamber 26 via passage 28 for inlet (ref. 7 in FIG. 1) and hence pass through the body part to entrain volatile liquid anaesthetic in the vaporising chamber. This first stream after passage through the vaporising chamber will find its way to outlet (Ref. 8 in FIG. 1) and into chamber 42 for mixing with a second or by-pass stream flowing through the valve casing 20. The second stream will leave the chamber 26 and enter the housing 30 through those inlet holes (33, 35, 37) in the wall 34 which are not blocked or covered by the valve body 32. The second stream will then pass from the housing 30 through the outlet hole 40 and into the chamber 42 where it will mix with the first stream. The united streams will then exit from the vaporiser at outlet 24.

Figure 6:
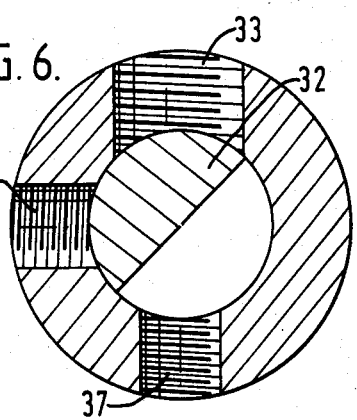
FIGS. 6, 7 and 8 are schematic cross-sections illustrating various positions of the valve member of FIG. 5 within a valve housing.
Figure 7:
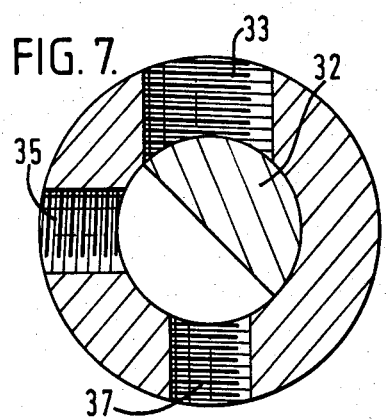
Figure 8:
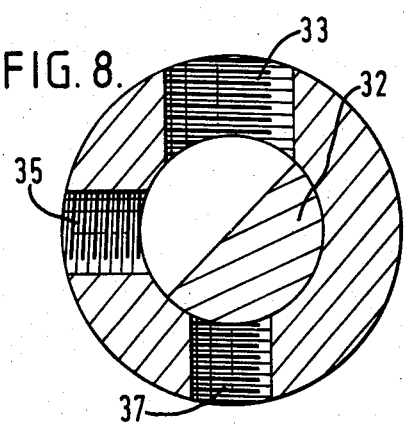

It will be evident from a perusal of FIGS. 6, 7 and 8 that by rotating the valve member 36 by means of the knob 48, the resistance to flow of the second stream through the valve casing 20 can be altered. As illustrated in FIG. 6, the position of the valve body 32 will block any flow of the second stream through holes 33 and 35 and proportionately there will be less flow of the second stream through the valve casing and proportionately more flow of the first stream through the body part 1.

FIGS. 7 illustrates an intermediate position and FIG. 8 a position at which there is minimum resistance to the flow of the second stream through the valve casing 20.

Although not illustrated, it will be evident that the position of the valve body 32 can be ascertained by the use of either markings on the knob and the upper surface of the cover 46 or by some form of indentation which will permit the operator to know when the valve body is in any one of the three positions illustrated in FIGS. 6 to 8.

A particular advantage of the embodiment described above is that for the user, whether it be a trained anaesthetist or nurse, the equipment is very simple and easy to operate in that there are clear positive settings which are not critically dependent on the position of the dial. Furthermore, the jets in the holes 33, 35 and 37 can be precisely machined with predetermined bore diameters and set at the time the vaporiser is manufactured and these are relatively tamper-proof.

The valve arrangement as described in the above embodiment is inexpensive to manufacture with the minimum of high precision parts. Furthermore, the large bores and the multiplicity of by-pass gas flow passages makes the equipment less likely to be affected by dust and the entry of foreign bodies.

The aforedescribed embodiment is eminently suitable for use with liquid analgesics such as ETHRANE (registered trade mark) for painful physiotherapy, burns, obstetrics and the like where the patient is conscious but requires the anaesthetic concentration which may be needed to be adjusted within limits according to circumstances. In such applications, great simplicity of apparatus is an advantage and the minimum of controls is essential.

I claim:

1. An anaesthetic vaporizer comprising a body part, said body part including a valve chamber and a vaporizing chamber for volatile liquid anaesthetic, a valve arrangement mounted within said valve chamber and dividing said valve chamber into an inlet portion and an outlet portion, a body part inlet communicating with said inlet portion for receiving carrier gas and a body part outlet communicating with said outlet portion for the passage therefrom of carrier gas together with entrained anaesthetic vapor, a vaporizing chamber inlet communicating between said inlet portion and said vaporizing chamber for receiving a first stream of carrier gas from said body part inlet and a vaporizing chamber outlet communicating between said vaporizing chamber and said outlet portion for delivering said carrier gas with entrained anaesthetic vapor to said body part outlet, said valve arrangement comprising a housing and a valve body rotatable within said housing, said housing having at least two spaced inlet openings communicating with said inlet portion and an outlet opening communicating with said outlet portion for passage therethrough of a second stream of carrier gas, said valve body rotatable to selectively cover and uncover one or more of said inlet openings to vary the resistance to flow of said second stream of carrier gas from said body part inlet to said body part outlet, each of said inlet openings including a removable jet having a bore of predetermined diameter, wherein said valve arrangement permits selective mixing of said second stream of carrier gas and said first stream of carrier gas and entrained anaesthetic vapor to control the mixture thereof from said body part outlet.

2. An anesthetic vaporizer as defined in claim 1, wherein there are three inlet openings angularly spaced about said housing, said housing being cylindrical in configuration and said valve body being a segmented cylinder in cross-section.

3. An anaesthetic vaporizer as defined in claim 1, in which said body part includes a cover enclosing said valve body within said body part, said valve body having a valve member extending through said cover for rotation by an operator.

* * * * *